US009026211B2

United States Patent
Yan et al.

(10) Patent No.: US 9,026,211 B2
(45) Date of Patent: May 5, 2015

(54) BATTERY CHARGER CIRCUIT FOR BATTERY POWERED IMPLANTABLE NEUROSTIMULATION SYSTEMS

(71) Applicant: Boston Scientific Neuromodulation Corporation, Valencia, CA (US)

(72) Inventors: Jie Yan, Valencia, CA (US); Yuping He, Northridge, CA (US); David K. L. Peterson, Saugus, CA (US); Rankiri T. Karunasiri, Castaic, CA (US); Joey Chen, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/274,442

(22) Filed: May 9, 2014

(65) Prior Publication Data
US 2014/0249603 A1 Sep. 4, 2014

Related U.S. Application Data

(63) Continuation of application No. 11/215,946, filed on Aug. 30, 2005, now abandoned.

(51) Int. Cl.
| | | |
|---|---|---|
| A61N 1/37 | (2006.01) | |
| A61N 1/378 | (2006.01) | |
| A61N 1/36 | (2006.01) | |
| H02J 7/02 | (2006.01) | |
| H02J 7/00 | (2006.01) | |
| H02J 5/00 | (2006.01) | |
| H02J 7/04 | (2006.01) | |

(52) U.S. Cl.
CPC .......... *A61N 1/3787* (2013.01); *A61N 1/36125* (2013.01); *H02J 7/025* (2013.01); *H02J 7/0068* (2013.01); *H02J 5/005* (2013.01); *H02J 7/045* (2013.01)

(58) Field of Classification Search
USPC ............ 607/33–34, 29, 27, 39, 46, 56, 60–61
See application file for complete search history.

(56) References Cited

U.S. PATENT DOCUMENTS

| | | |
|---|---|---|
| 4,082,097 A | 4/1978 | Mann et al. |
| 4,599,523 A | 7/1986 | Pless et al. |
| 5,411,537 A | 5/1995 | Munshi et al. |
| 5,557,210 A | 9/1996 | Cappa et al. |
| 5,584,863 A | 12/1996 | Rauch et al. |
| 5,602,460 A | 2/1997 | Fernandez et al. |
| 5,679,022 A | 10/1997 | Cappa et al. |
| 5,733,313 A | 3/1998 | Barreras et al. |
| 5,769,877 A | 6/1998 | Barreras et al. |
| 5,807,397 A | 9/1998 | Barreras et al. |
| 5,904,705 A | 5/1999 | Kroll et al. |
| 6,067,474 A | 5/2000 | Schulman et al. |
| 6,272,382 B1 | 8/2001 | Faltys et al. |
| 6,350,263 B1 | 2/2002 | Wetzig et al. |
| 6,393,325 B1 | 5/2002 | Mann et al. |
| 6,516,227 B1 | 2/2003 | Meadows et al. |
| 6,553,262 B1 | 4/2003 | Lang et al. |
| 6,553,263 B1 | 4/2003 | Meadows et al. |
| 6,826,430 B2 | 11/2004 | Faltys et al. |

*Primary Examiner* — Paula J Stice
(74) *Attorney, Agent, or Firm* — Lewis & Reese, PLLC

(57) ABSTRACT

An implantable device includes a stimulation electronic circuit, a battery, a receiver configured to receive energy from a source external to the implantable stimulation device, and a battery charger circuit configured to use the energy to charge the battery and power the stimulation electronic circuit, the battery charger circuit including a load switch for connecting/disconnecting the battery, the load switch being controlled by the stimulation electronic circuit.

15 Claims, 3 Drawing Sheets

BATTERY CHARGER CIRCUIT FOR BATTERY POWERED IMPLANTABLE NEUROSTIMULATION SYSTEMS

CROSS-REFERENCE TO RELATED APPLICATIONS

This is a continuation of U.S. patent application Ser. No. 11/215,946, filed Aug. 30, 2005, which is incorporated here by reference in its entirety, and to which priority is claimed.

TECHNICAL FIELD

The invention relates generally to neurostimulation systems and, in particular, to a battery charger circuit for a battery powered implantable neurostimulation system.

BACKGROUND ART

Implantable neurostimulation systems generate electrical stimuli to body nerves and tissues for the therapy of biological disorders, such as Spinal Cord Stimulation Systems to treat chronic pain, Cochlear Stimulation Systems to treat deafness, and Deep Brain Stimulation Systems to treat motor and psychological disorders, etc. All of the implantable stimulation systems need energy to operate and generate stimulation. The energy usually comes from an external power source or from an implanted battery. For neurostimulation systems powered by the external device, an external power device is needed to be continuously worn to power the implanted devices. Some neurostimulation systems utilize an implanted battery to provide power for stimulation. An example of one such neurostimulation system is disclosed in U.S. Pat. No. 6,516,227. The rechargeable spinal cord stimulation system with an implanted lithium-ion battery achieves longer operation lifetime and smaller device size. The implanted battery needs to be recharged occasionally to maintain sufficient energy to power the stimulation electronic circuitry. In U.S. Pat. No. 6,516,227, an off-the-shelf, linear regulation battery charger integrated circuit (IC) available from Linear Technology as part number LTC1731-4.1 is used to receive power through inductive coupling from an external charging system and to provide proper charge current and voltage for the battery.

In addition, as described in U.S. Pat. No. 6,516,227, if the battery has been discharged below a certain voltage level or completely discharged to zero volts, the rechargeable spinal cord stimulation system will temporarily shut off the stimulation. It may take up to two hours to charge the battery to a capacity that allows stimulation to be resumed again. This means patients may have to wait some time until the battery is charged enough to provide stimulation again.

U.S. Pat. No. 5,769,877 discloses an implantable device with a capacitive replenishable power source that is able to replenish and simultaneously deliver stimulating pulses to targeted tissues.

U.S. Pat. No. 6,272,382 discloses a fully implantable cochlear stimulator (ICS) system with an implanted rechargeable battery and an external battery charger (EBC). As described in this patent, in the event the implanted battery within the implantable speech processor (ISP) module malfunctions, or for whatever reason cannot be used, or the user or clinician (or other medical personnel) does not want to use it, it is still possible, through use of the EBC to provide operating power to the ISP module and ICS module so that they may continue to function for their intended purpose (e.g., stimulating and/or sensing). By having such a backup option available, the patient may delay battery-replacement and/or corrective surgery indefinitely.

U.S. Pat. No. 6,826,430 discloses a fully implantable cochlear prosthesis that includes an implantable housing with a charger 33. As described in this patent, an RF coil 30 receives power and may transmit back telemetry data. The received power is rectified by diode D1 and powers a linear Lithium Ion Battery Charger 33 to charge an implanted battery 34. A Battery Protection Circuit 35 protects the battery from conditions such as over charge and over-discharge, automatically disconnecting the source or load when necessary. The system can still operate from an external source through the coil 30 if the battery is disconnected. A Buck Converter Circuit(s) 36 derives the necessary power supply voltages from the battery voltage that are required for operation of the prosthesis.

It would be desirable to be able to provide a battery charger circuit that permits externally transmitted power to be used for charging an implanted battery and powering a stimulation circuit, and which is controlled by the stimulation circuit and can be used to power the stimulation circuit when the implanted battery is disconnected, defective, or determined to not be suitable for use.

It would further be desirable to be able to provide a battery powered implantable neurostimulation system with a battery charger circuit that is easily integrated with modern integrated circuits technology, such as CMOS N-well integrated circuits technology.

It would further be desirable to be able to provide a battery powered implantable neurostimulation system with a battery charger circuit that is configured to charge an implanted battery depending upon a specification characteristic of the battery.

SUMMARY OF THE INVENTION

The battery charger circuit described herein is part of an implantable battery powered neurostimulation system. In an example embodiment, the battery charger circuit provides energy to charge the battery from an external source, and can also simultaneously power a stimulation electronic circuit independent of the battery voltage. Therefore, and beneficially, the patient does not need to wait several hours until the battery is sufficiently charged for stimulation.

For some implantable stimulation systems, while the fitting/programming process is executed, it may be necessary to disconnect the rechargeable battery in order to protect the patient in the event of a failure. The battery charger circuit described herein provides a mechanism for electrically disconnecting the battery and for powering the stimulation electronic circuitry using an energy source external to the implanted system. In an example embodiment, if the battery loses its charging capability over time, the battery charger circuitry can be used as an alternative power source to power the stimulation electronic circuitry through inductive coupling from an external charging system so that the implantable neurostimulation system is not required to be explanted.

In an example embodiment, an implantable device includes a stimulation electronic circuit, a battery (e.g., a Lithium-Ion battery), a receiver (e.g., a RF power receiver) configured to receive energy from a source external to the implantable stimulation device, and a battery charger circuit configured to use the energy to charge the battery and power the stimulation electronic circuit, the battery charger circuit including a load switch for connecting/disconnecting the battery, the load switch being controlled by the stimulation electronic circuit. In an example embodiment, the battery charger circuit is configured to power the stimulation electronic circuit when the battery is disconnected from the stimulation electronic circuit. In an example embodiment, the battery charger circuit is configured to simultaneously charge the battery and power the stimulation electronic circuit. In an example embodiment, the battery charger circuit includes a load voltage regulator which allows the stimulation electronic circuit to be powered by the battery charger circuit alone without the battery. In an example embodiment, the battery charger circuit includes a charging circuit (e.g., including current limited voltage regulators) configured to charge the battery in multiple charge modes. In an example embodiment, the load switch is configured to provide an interface compatible with CMOS N-well integrated circuit technology. In an example embodiment, the load switch is implemented as a PMOS transistor. In an example embodiment, a substrate of the PMOS transistor is electrically connected to a voltage output of the receiver when the external source is providing energy to the receiver, and to a voltage output of the battery when the external source is not present.

In an example embodiment, an implantable device includes a stimulation electronic circuit, a battery, a receiver configured to receive energy from a source external to the implantable stimulation device, and a battery charger circuit configured to use the energy to charge the battery and power the stimulation electronic circuit, the battery charger circuit including a load switch for connecting/disconnecting the battery, the load switch being configured to provide an interface compatible with CMOS N-well integrated circuit technology. In an example embodiment, the battery charger circuit is configured to power the stimulation electronic circuit when the battery is disconnected from the stimulation electronic circuit. In an example embodiment, the load switch is implemented as a PMOS transistor. In an example embodiment, the load switch is controlled by the stimulation electronic circuit. In an example embodiment, the battery charger circuit includes a load voltage regulator which allows the stimulation electronic circuit to be powered by the battery charger circuit alone without the battery. In an example embodiment, the battery charger circuit includes a charging circuit configured to charge the battery in multiple charge modes.

In an example embodiment, an implantable charger for a battery of an implantable stimulation device includes a receiver configured to receive energy from a source external to the implantable stimulation device, and circuitry configured to use the energy to charge the battery depending upon a specification characteristic of the battery, and to power the implantable stimulation device when the battery is disconnected from the implantable stimulation device. In an example embodiment, the specification characteristic is a trickle charge voltage threshold. In an example embodiment, the circuitry is configured to charge the battery in multiple charge modes. In an example embodiment, the multiple charge modes include a trickle charge mode which charges the battery with a constant current until a voltage of the battery rises above a threshold. In an example embodiment, the multiple charge modes include a normal charge mode which charges the battery with a constant current when a battery voltage is above a trickle charge voltage threshold and below a constant charge voltage threshold, and thereafter with a constant voltage until a charge current decreases to an end of charge limit, which may be, e.g., substantially zero. In an example embodiment, the charger for a battery of an implantable stimulation device further includes a delay cell to smooth a transition between two of the charge modes.

BRIEF DESCRIPTION OF THE DRAWINGS

Detailed description of embodiments of the invention will be made with reference to the accompanying drawings.

DETAILED DESCRIPTION

The following is a detailed description for carrying out embodiments of the invention. This description is not to be taken in a limiting sense, but is made merely for the purpose of illustrating the general principles of the example embodiments of the invention.

Figure 1:
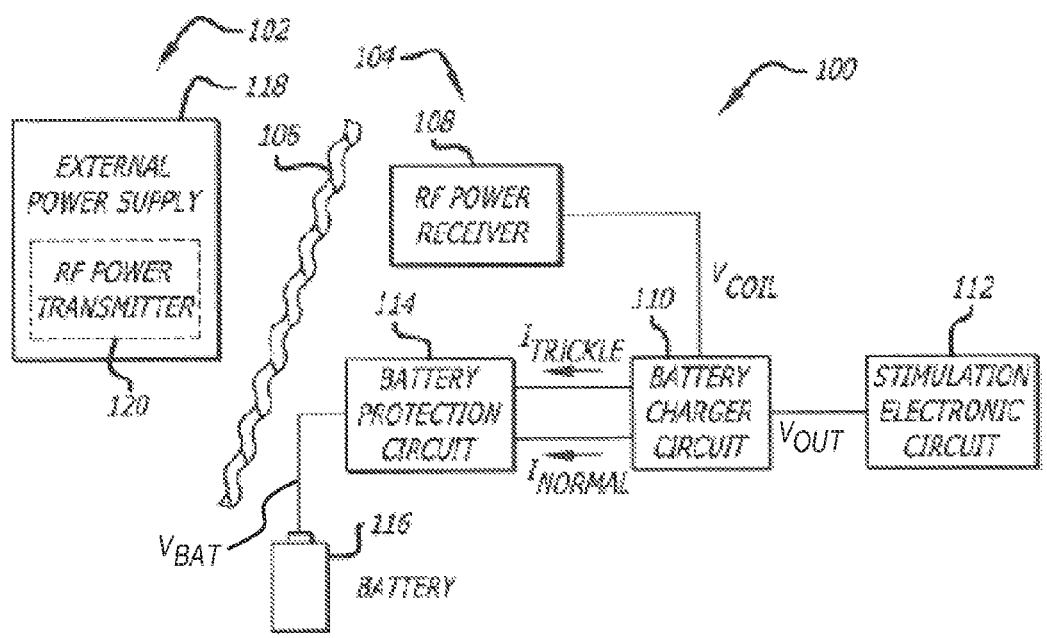
FIG. 1 illustrates an example embodiment of an implantable neurostimulation system.

Referring to FIG. 1, in an example embodiment, an implantable neuro stimulation system 100 includes an external portion 102 and an internal portion 104 positioned on opposite sides of a tissue barrier 106 (such as a layer of skin). In use, the internal portion 104 is implanted within the patient beneath the tissue barrier 106 (in a manner generally determined by the nature of the stimulation to be provided). In this example embodiment, the internal portion 104 includes a RF power receiver 108, a battery charger circuit 110, a stimulation electronic circuit 112, a battery protection circuit 114 and a battery 116 (e.g., a rechargeable Lithium-Ion battery) configured as shown. In this example embodiment, the external portion 102 includes an external power supply 118 with a RF power transmitter 120. Power is generated by the power supply 118 and applied to the battery charger circuit 110. More specifically, incoming energy induces AC voltage in a coil of the RF power receiver 108. The RF power receiver 108 converts the induced AC voltage to a fixed DC Voltage as Vcoil. As described below in greater detail, the battery charger circuit 110 provides a charging function in addition to powering the stimulation electronic circuit 112. The battery protection circuit 114 monitors battery voltage and current, and in the event of a fault, disconnects the battery 116 from the circuit.

Figure 2:
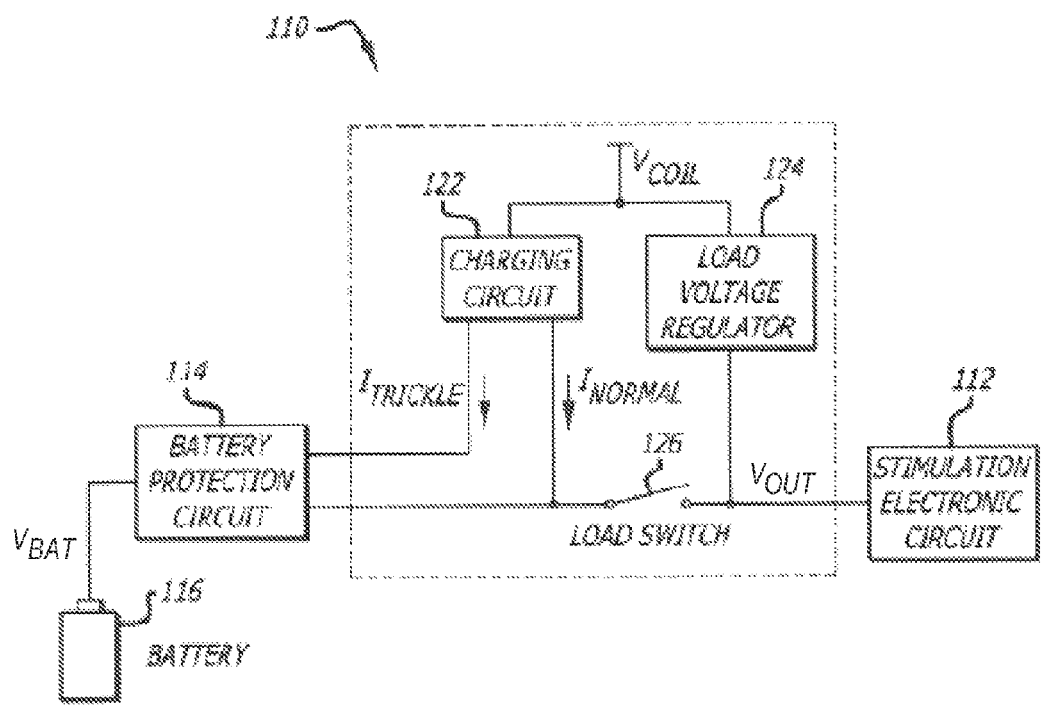
FIG. 2 illustrates an example embodiment of the battery charger circuit of FIG. 1.

Referring to FIG. 2, in an example embodiment, the battery charger circuit 110 includes a charging circuit 122, a load voltage regulator 124 and a load switch 126, configured as shown. In an example embodiment, the charging circuit 122 is configured to provide the required charging current and voltage to charge the battery 116 according to the battery specification. By way of example, if the battery voltage is below a trickle charge voltage (e.g. 2.7V), a fixed trickle charge current Itrickle (usually in the range of C/10, where C indicates the capacity of the battery) is provided on the trickle charge path. If the battery voltage is higher than the trickle charge voltage level, a Constant Current (CC) Inormal is provided on the normal charge path. The load voltage regulator 124 is used to power the stimulation electronic circuit 112 when the battery is disconnected or dead. The load voltage regulator 124 allows the stimulation electronic circuit 112 to be powered by the battery charger circuit 110 alone without the battery 116. The load switch 126 is used to control the connection/disconnection of the battery 116.

Figure 3:
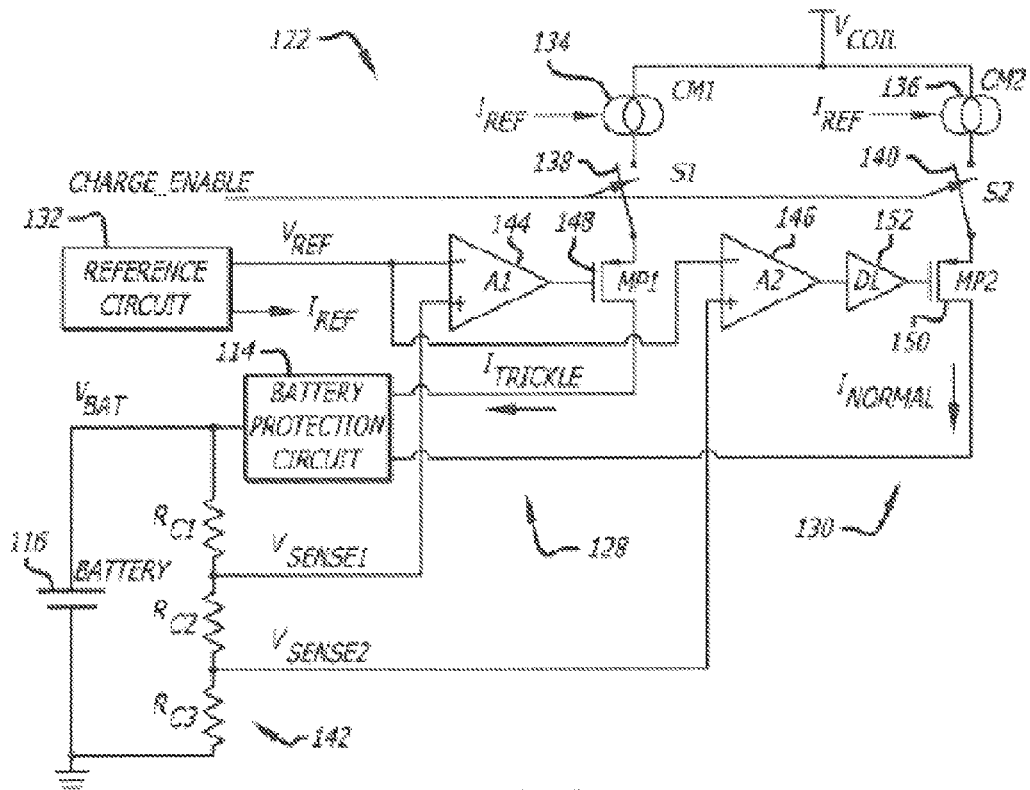
FIG. 3 illustrates an example embodiment of the charging circuit of FIG. 2.

Referring to FIG. 3, in an example embodiment, the charging circuit 122 includes two current limited voltage regulators. A first current limited voltage regulator 128 provides trickle charge current Itrickle, and a second current limited voltage regulator 130 provides normal charge current Inormal. In this example embodiment, the charging circuit 122 includes a reference circuit 132 which generates reference voltage VREF and reference current IREF. In this example embodiment, a first current mirror pair CM1 134 amplifies IREF and generates the trickle charge current Itrickle which is for example C/10, where C indicates the capacity of the battery. In this example embodiment, a second current mirror pair CM2 136 amplifies IREF and generates the normal charge current Inormal which is for example in the range of C/5 to C/2, where C indicates the capacity of the battery. In operation, charging begins when the Charge Enable signal is asserted, which closes a first switch S1 138 and a second switch S2 140. In this example embodiment, the charging circuit 122 includes a resistor divider 142 formed by resistors RC1, RC2, and RC3 configured as shown. The resistor divider 142 senses the battery voltage Vbat and generates sense voltages Vsense1 and Vsense2 which are fractions of the battery voltage Vbat determined by the values of the resistors RC1, RC2, and RC3. The voltages Vsense1 and Vsense2 are compared with the reference voltage VREF by a first amplifier A1 144 and a second amplifier A2 146, respectively. The outputs of A1 and A2 serve as the control signals for a first series-regulating transistor MP1 148 and a second series-regulating transistor MP2 150, respectively. In this example embodiment, the resistor divider 142, amplifier A1 144, series-regulating transistor MP1 148, and current mirror pair CM1 134 form the current limited voltage regulator 128 for trickle charge function. In this example embodiment, the resistor divider 142, amplifier A2 146, series-regulating transistor MP2 150, and current mirror pair CM2 136 form the current limited voltage regulator 130 for normal charge function.

Figure 6:
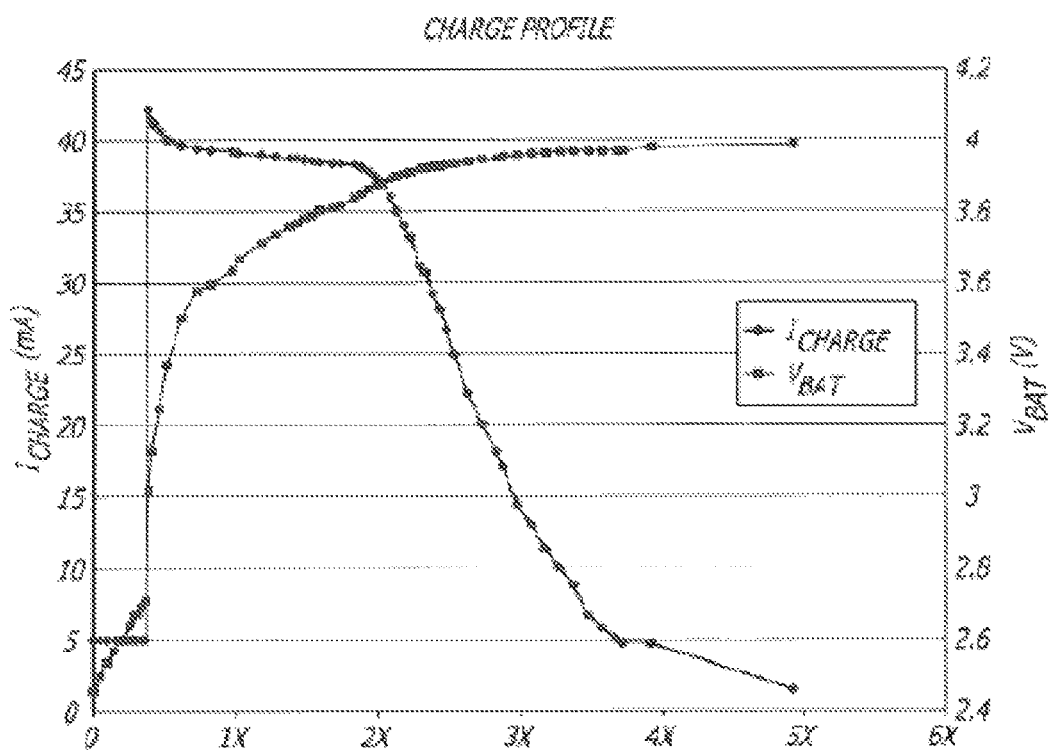
FIG. 6 is an example charge profile plot showing charge current and battery voltage over time.

At the beginning of the charge cycle in this example embodiment, if the battery voltage is below the trickle charge voltage threshold, the charging circuit 122 (e.g., provided as an IC) goes into a trickle charge mode. In this example embodiment, the charging circuit 122 goes into a normal charge mode after the battery voltage rises above the trickle charge voltage threshold. By way of example, and referring to FIG. 6, when the battery voltage Vbat is below the trickle charge voltage threshold (e.g., 2.7V), the charging circuit 122 goes into trickle charge mode and charges the battery at a charge current Icharge of 5 mA. The charging circuit 122 goes into the normal charge mode after the battery voltage rises above the trickle charge voltage threshold and charges the battery at a charge current Icharge (e.g., 40 mA). When the battery voltage is charged to a constant charge voltage threshold (e.g., 3.9V), the charging circuit 122 goes into constant voltage mode until the charge current decreases to an end of charge limit, which may be, e.g., substantially zero.

Referring again to FIG. 3, it should be appreciated that the charging circuit 122 can be configured in other ways, for example, to switch between charge modes using a different threshold which can be (but is not necessarily) derived from the battery specification. Other criteria can also be used to determine how and when the charging circuit 122 will transition from one charge mode to another. Moreover, the charging circuit 122 can be configured to provide only a single charge mode, or to provide more than two different charge modes.

In this example embodiment, in the normal charging mode, the battery 116 is charged in two further modes, namely, a Constant Current (CC)-mode when the cell voltage is above a trickle charge voltage threshold and below a constant charge voltage threshold and then in a Constant Voltage (CV)-mode until the charge current decreases to an end of charge limit, which may be, e.g., substantially zero. In CC-mode, the voltage at the gate of the regulating transistor MP2 150 is close to ground, and the regulating transistor MP2 150 is fully opened and the charging current goes to the battery 116. In CV-mode, the voltage at the gate of the regulating transistor MP2 150 is close to Vcoil minus the voltage drop across CM2 136 and S2 140, and the charging current that goes to the battery 116 is gradually reduced and charging is stopped finally. In this example embodiment, the charging circuit 122 includes a delay cell DL 152 which helps smooth the transition from trickle charge mode to normal charge mode.

Figure 4:
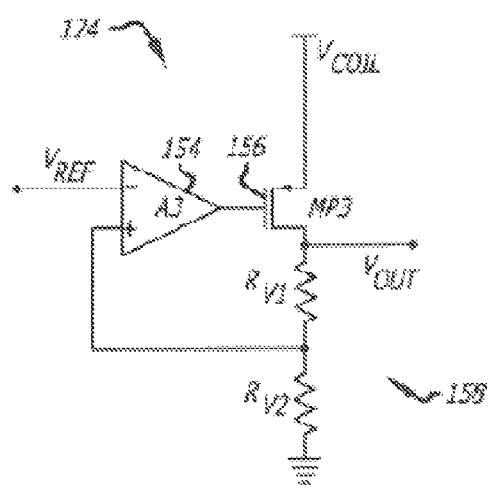
FIG. 4 illustrates an example embodiment of the load voltage regulator of FIG. 2.

Referring to FIG. 4, in an example embodiment, the load voltage regulator 124 is implemented as a linear regulator which includes an amplifier A3 154, a PMOS pass transistor MP3 156 and a voltage divider 158 (RV1 and RV2), configured as shown. In this example embodiment, the load voltage regulator 124 converts the input voltage Vcoil to a fixed optimum operating voltage VOUT (e.g., 3.6V) and supplies the operating voltage to power the stimulation electronic circuit 112 alone when the battery is disconnected or defective. In an example embodiment, the load voltage regulator 124 supplies voltage and current to the stimulation electronic circuit 112 based on the stimulation need.

Figure 5:
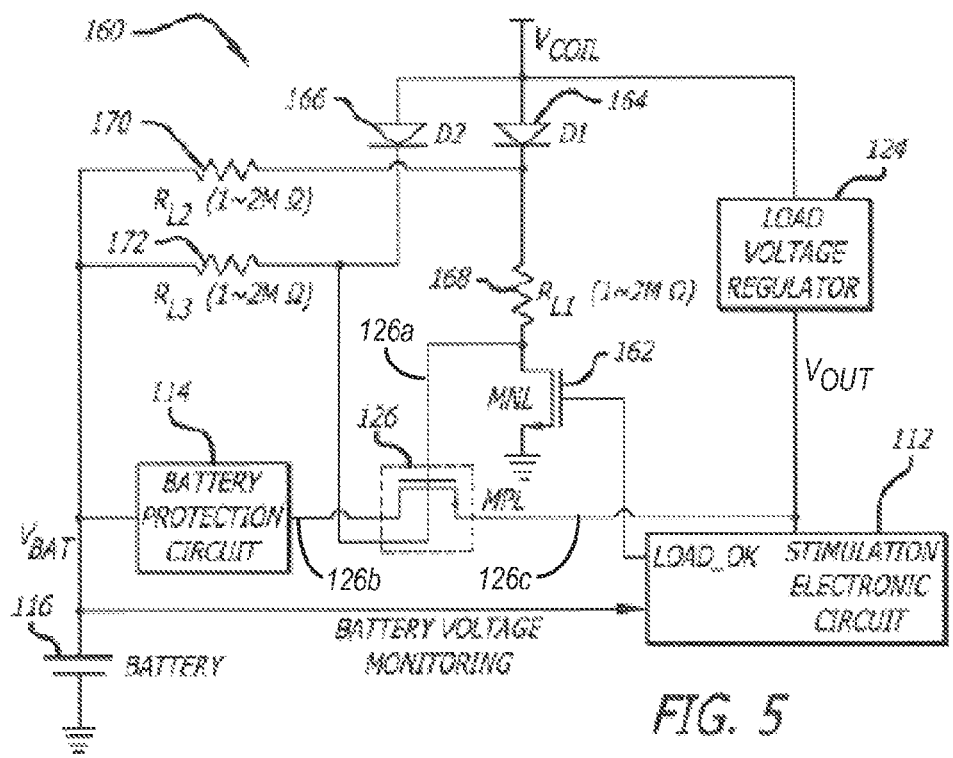
FIG. 5 illustrates an example embodiment of the load switch of FIG. 2 and its control circuitry.

Referring to FIG. 5, in an example embodiment, the load switch 126 is controlled at terminal 126a by the stimulation electronic circuit 112. In this example embodiment, the stimulation electronic circuit 112 monitors the battery voltage and provides a control signal Load_OK to the load switch 126. In an example embodiment, the load switch 126 is normally open between terminals 126b and 126c, and is only closed when the battery voltage is close to the output voltage of the load voltage regulator 124 which prevents additional current from the load voltage regulator 124 from flowing into the battery 116. For normal operation, the load switch 126 must be closed before the external power supply 118 is removed to connect the stimulation electronic circuit 112 to the battery 116. In an example embodiment, if the battery voltage is lower than the level the stimulation electronic circuit 112 can operate at, the stimulation electronic circuit 112 shuts itself off before the external power supply 118 is applied.

In an example embodiment, the load switch 126 is implemented as a PMOS transistor MPL, and control circuitry 160 (for the load switch 126) is configured as shown in FIG. 5. When Load_OK is low, in this example embodiment, a NMOS transistor MNL 162 is off so the gate of PMOS transistor MPL 126 is pulled high and the load switch 126 is off. When Load_OK is high, NMOS transistor MNL 162 is on so the gate of PMOS transistor MPL 126 is pulled low and the load switch 126 is on. In an example embodiment, the substrate of the PMOS transistor MPL 126 is always tied to the highest voltage potential of the charger circuit so that the substrate diode is always reverse biased to avoid current leakage. In an example embodiment, the substrate of the PMOS transistor MPL 126 is hooked (electrically connected) to one diode drop below Vcoil if the external power supply 118 is present, or to the battery voltage if the external power supply 118 is not present. In this example embodiment, two diodes 164 and 166 (D1 and D2) are used to prevent the reverse current from the battery. Alternatively, the diodes D1 and D2 can be replaced with transistors configured to function substantially as diodes. In this example embodiment, three resistors 168, 170, and 172 (RL1, RL2 and RL3) in Mega Ohms range are used as shown to prevent direct current flowing from Vcoil to the battery.

Although the present invention has been described in terms of the example embodiments above, numerous modifications and/or additions to the above-described embodiments would be readily apparent to one skilled in the art. It is intended that the scope of the present invention extends to all such modifications and/or additions.

What is claimed is:

1. An implantable device, comprising:
   a battery having a battery voltage;
   a receiver configured to receive energy from a source external to the implantable device and to produce a DC voltage;
   a regulator for receiving the DC voltage and configured to produce an output voltage from the DC voltage at a node, wherein the node is configured to power a load in the implantable device;
   a charging circuit for receiving the DC voltage and configured to charge the battery using the DC voltage; and
   a switch configured to receive the battery voltage at a first terminal, and coupled to the node at a second terminal,
   wherein the switch is controllable at a third terminal to couple the battery voltage to the node.

2. The device of claim 1, further comprising a battery protection circuit, wherein the charging circuit is configured to charge the battery through the battery protection circuit.

3. The device of claim 2, wherein the switch receives the battery voltage at the first terminal through the battery protection circuit.

4. The device of claim 1, further comprising a battery protection circuit, wherein the switch receives the battery voltage at the first terminal through the battery protection circuit.

5. The device of claim 1, wherein the output voltage produced by the regulator comprises a fixed optimum operating voltage for the load.

6. The device of claim 1, wherein the charging circuit is configured to charge the battery via first and second charging paths.

7. The device of claim 6, wherein the first charging path is activated if the battery voltage is below a threshold, and wherein the second charging path is activated if the battery voltage is above a threshold.

8. The device of claim 1, wherein the charging circuit is configured to trickle charge the battery if the battery voltage is below a first threshold, and to charge the battery in a constant current mode if the battery voltage is above the first threshold.

9. The device of claim 8, wherein the charging circuit is configured to charge the battery in a constant voltage mode if the battery voltage is above a second threshold higher than the first threshold.

10. The device of claim 1, wherein the switch comprises a PMOS transistor.

11. The device of claim 10, wherein a substrate of the PMOS transistor is electrically connected to the DC voltage if the external source is providing energy to the receiver, or electrically connected to the battery voltage if the external source is not providing energy to the receiver.

12. The device of claim 1, wherein the load comprises a stimulation circuit for providing neurostimulation to a patient.

13. The device of claim 1, wherein the switch is controllable at the third terminal by the load.

14. The device of claim 1, wherein the switch is controllable at the third terminal to couple the battery voltage to the node if the external source is not present.

15. The device of claim 1, wherein the DC voltage is used by the regulator and the charging circuit to power the load and to charge the battery simultaneously.

* * * * *